(12) United States Patent
Hartig et al.

(10) Patent No.: US 7,763,280 B2
(45) Date of Patent: Jul. 27, 2010

(54) TIOTROPIUM CONTAINING POWDER FORMULATION FOR INHALATION

(75) Inventors: Mareke Hartig, Ingelheim (DE); Michael Trunk, Ingelheim (DE); Michael Walz, Bingen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 1505 days.

(21) Appl. No.: 10/718,404

(22) Filed: Nov. 20, 2003

(65) Prior Publication Data

US 2004/0136919 A1 Jul. 15, 2004

Related U.S. Application Data

(60) Provisional application No. 60/446,669, filed on Feb. 11, 2003.

(30) Foreign Application Priority Data

Nov. 28, 2002 (DE) .................. 102 55 387

(51) Int. Cl.
*A61K 9/50* (2006.01)
(52) U.S. Cl. ........................................ 424/499
(58) Field of Classification Search ........... None
See application file for complete search history.

(56) References Cited

U.S. PATENT DOCUMENTS

| | | |
|---|---|---|
| 3,634,582 A | 1/1972 | Hartley et al. |
| 3,758,476 A | 9/1973 | Rippel et al. |
| 3,860,618 A | 1/1975 | Hartley et al |
| 3,957,965 A | 5/1976 | Hartley et al. |
| 4,009,280 A | 2/1977 | Macarthur et al. |
| 4,042,700 A | 8/1977 | Banholzer et al. |
| 4,608,377 A | 8/1986 | Banholzer et al. |
| 4,783,534 A | 11/1988 | Banholzer |
| 5,478,578 A | 12/1995 | Arnold et al. |
| 5,498,422 A | 3/1996 | Nakamichi et al. |
| 5,562,918 A | 10/1996 | Stimpson |
| 5,610,163 A | 3/1997 | Banholzer et al. |
| 5,641,510 A | 6/1997 | Clark et al. |
| 5,654,314 A | 8/1997 | Banholzer et al. |
| 5,770,738 A | 6/1998 | Banholzer et al. |
| 5,947,118 A | 9/1999 | Hochrainer et al. |
| 5,952,505 A | 9/1999 | Banholzer |

(Continued)

FOREIGN PATENT DOCUMENTS

CA   2436537 A1   5/2002

(Continued)

OTHER PUBLICATIONS

Chemical Abstract for FR 8142 M: Derwent 1966-36583F [00].

(Continued)

*Primary Examiner*—Carlos A Azpuru
(74) *Attorney, Agent, or Firm*—Michael P. Morris; Mary-Ellen M. Devlin; Wendy A. Petka (57) ABSTRACT

The invention relates to powdered preparations containing tiotropium for inhalation, processes for preparing them as well as their use in preparing a pharmaceutical composition for the treatment of respiratory complaints, particularly for the treatment of COPD (chronic obstructive pulmonary disease) and asthma.

2 Claims, 1 Drawing Sheet

U.S. PATENT DOCUMENTS

| | | | |
|---|---|---|---|
| 6,228,394 B1 * | 5/2001 | Horhota et al. | 424/456 |
| 6,235,725 B1 * | 5/2001 | Ahmed | 514/56 |
| 6,284,287 B1 | 9/2001 | Sarlikiotis et al. | |
| 6,418,926 B1 | 7/2002 | Chawla | |
| 6,482,429 B1 | 11/2002 | Etzler | |
| 6,486,321 B2 | 11/2002 | Banholzer et al. | |
| 6,506,900 B1 | 1/2003 | Banholzer et al. | |
| 6,517,865 B2 | 2/2003 | Cade et al. | |
| 6,585,959 B2 | 7/2003 | Walz et al. | |
| 6,589,536 B1 | 7/2003 | Brox et al. | |
| 6,623,760 B1 * | 9/2003 | Yang et al. | 424/489 |
| 6,645,466 B1 | 11/2003 | Keller et al. | |
| 6,773,895 B2 | 8/2004 | Jung et al. | |
| 6,881,422 B2 | 4/2005 | Banholzer et al. | |
| 6,919,325 B2 | 7/2005 | Linz et al. | |
| RE38,912 E | 12/2005 | Walz et al. | |
| 2001/0008637 A1 | 7/2001 | Hochrainer et al. | |
| 2002/0110529 A1 | 8/2002 | Bechtold-Peters et al. | |
| 2002/0183292 A1 | 12/2002 | Pairet et al. | |
| 2002/0193392 A1 | 12/2002 | Schmelzer et al. | |
| 2002/0193393 A1 | 12/2002 | Pairet et al. | |
| 2003/0008001 A1 | 1/2003 | Wachtel et al. | |
| 2003/0043687 A1 | 3/2003 | Boeck et al. | |
| 2003/0068278 A1 | 4/2003 | Boeck et al. | |
| 2003/0070679 A1 | 4/2003 | Hochrainer et al. | |
| 2003/0125350 A1 | 7/2003 | Hassan et al. | |
| 2003/0202944 A1 | 10/2003 | Staniforth | |
| 2003/0235538 A1 | 12/2003 | Zierenberg | |
| 2004/0019073 A1 | 1/2004 | Drechsel et al. | |
| 2004/0024007 A1 | 2/2004 | Pairet et al. | |
| 2004/0029907 A1 | 2/2004 | Banholzer et al. | |
| 2004/0136919 A1 | 7/2004 | Hartig et al. | |
| 2004/0176338 A1 | 9/2004 | Pairet et al. | |
| 2005/0009857 A1 | 1/2005 | Banholzer et al. | |
| 2005/0084457 A1 | 4/2005 | Hochrainer et al. | |
| 2005/0148562 A1 | 7/2005 | Pairet et al. | |
| 2005/0256149 A1 | 11/2005 | Linz et al. | |
| 2006/0039868 A1 | 2/2006 | Bechtold-Peters et al. | |
| 2006/0251586 A1 | 11/2006 | Zierenberg | |
| 2006/0292084 A1 | 12/2006 | Wachtel et al. | |
| 2007/0128125 A1 | 6/2007 | Schmelzer et al. | |

FOREIGN PATENT DOCUMENTS

| | | |
|---|---|---|
| EP | 0 418 716 A1 | 3/1991 |
| EP | 1238661 A1 | 9/2002 |
| GB | 1242211 A | 8/1971 |
| WO | WO 93/11746 A1 | 6/1993 |
| WO | WO 94/28958 | 12/1994 |
| WO | WO 95/11666 A1 | 5/1995 |
| WO | WO 96/02231 A1 | 2/1996 |
| WO | 9936116 A1 | 7/1999 |
| WO | WO 00/28979 A1 | 5/2000 |
| WO | WO 00/47200 A1 | 8/2000 |
| WO | WO 02/30389 A1 | 4/2002 |
| WO | WO 02/30390 A2 | 4/2002 |
| WO | 0236163 A2 | 5/2002 |
| WO | WO 02/098874 A2 | 12/2002 |
| WO | WO 03/017970 A1 | 3/2003 |
| WO | WO 03/084502 A1 | 10/2003 |
| WO | WO 03/084509 A1 | 10/2003 |

OTHER PUBLICATIONS

N.H. Shah, et al. "Elasticity of Soft Gelatin Capsules Containing Polyethylene Glycol 400—Quantitation and Resolution" Pharmaceutical Technology, Mar. 1992, p. 126-133.

M. Walz, et al. "Process for Preparing Powder Formulations" U.S. Appl. No. 10/766,648, filed Jan. 28, 2004.

Aulton, Michael E.,, "Packaging Technology;" Pharmaceutics: The Sceince of Dosage Form Design, Churchill Livingstone, 1988, p. 712-721.

Gennaro, Alfonso R. et al editors, Remington: The Science and Practice of Pharmacy; 29th Edition, 2000; p. 1012 Chapter 54.

Jenkins and Osborn: "Results of Package Evaluations," Packaging drugs and pharmaceuticals; Technomic Publishing Co., 1994, pp. 256-258.

Steckel and Mueller; "In vitro evaluation of dry powder inhalers II: influence of carrier particle size and concentration on in vitro peposition" Int'l Journal of Pharmaceutics 154 (1997) 31-37.

Wade and Weller: "Lactose" Handbook of Pharmaceutical Excipients, Second Edition, American Pharmaceutical Assoc. and The Pharmaceutical Press, 1994, P252-261.

Zeng, X.M., et al: Lactose as a carrier in dry powder formulations, Journal of Pharmaceutical Sciences, vol. 90, No. 9, Sep. 2001 - p. 1424-1434.

Zeng, X.M., et al; "Particulate Interations in Dry Powder Formulations for Inhalation"; Department of Pharmacy, King's College London, 2001; Contents and pp. 1424-1434.

* cited by examiner

FIG. 1.

TIOTROPIUM CONTAINING POWDER FORMULATION FOR INHALATION

RELATED APPLICATIONS

Benefit of U.S. Provisional Application Ser. No. 60/446,669, filed on Feb. 11, 2003 is hereby claimed.

FIELD OF THE INVENTION

The invention relates to powdered preparations containing tiotropium for inhalation, processes for preparing them as well as their use for preparing a pharmaceutical composition for treating respiratory complaints, particularly for treating COPD (chronic obstructive pulmonary disease) and asthma.

BACKGROUND TO THE INVENTION

Tiotropium bromide is known from European Patent Application EP 418 716 A1 and has the following chemical structure:

Tiotropium bromide is a highly effective anticholinergic with a long-lasting activity which can be used to treat respiratory complaints, particularly COPD (chronic obstructive pulmonary disease) and asthma. The term tiotropium refers to the free ammonium cation.

For treating the abovementioned complaints, it is useful to administer the active substance by inhalation. In addition to the administration of broncholytically active compounds in the form of metered aerosols and inhalable solutions, the use of inhalable powders containing active substance is of particular importance.

With active substances which have a particularly high efficacy, only small amounts of the active substance are needed per single dose to achieve the desired therapeutic effect. In such cases, the active substance has to be diluted with suitable excipients in order to prepare the inhalable powder. Because of the large amount of excipient, the properties of the inhalable powder are critically influenced by the choice of excipient. When choosing the excipient its particle size is particularly important. As a rule, the finer the excipient, the poorer its flow properties. However, good flow properties are a prerequisite for highly accurate metering when packing and dividing up the individual doses of preparation, e.g. when producing capsules (inhalettes) for powder inhalation or when the patient is metering the individual dose before using a multi-dose inhaler. Moreover, the particle size of the excipient is very important for the emptying characteristics of capsules when used in an inhaler. It has also been found that the particle size of the excipient has a considerable influence on the proportion of active substance in the inhalable powder which is delivered for inhalation. The term inhalable proportion of active substance refers to the particles of the inhalable powder which are conveyed deep into the branches of the lungs when inhaled with a breath. The particle size required for this is between 1 and 10 μm, preferably less than 6 μm.

The aim of the invention is to prepare an inhalable powder containing tiotropium which, while being accurately metered (in terms of the amount of active substance and powder mixture packed into each capsule by the manufacturer as well as the quantity of active substance released and delivered to the lungs from each capsule by the inhalation process) with only slight variations between batches, enables the active substance to be administered in a large inhalable proportion. A further aim of the present invention is to prepare an inhalable powder containing tiotropium which ensures good emptying characteristics of the capsules, whether it is administered to the patient using an inhaler, for example, as described in WO 94/28958, or in vitro using an impactor or impinger. The fact that tiotropium, particularly tiotropium bromide, has a therapeutic efficacy even at very low doses imposes further conditions on an inhalable powder which is to be used with highly accurate metering. Because only a low concentration of the active substance is needed in the inhalable powder to achieve the therapeutic effect, a high degree of homogeneity of the powder mixture and only slight fluctuations in the dispersion characteristics from one batch of capsules to the next are essential. The homogeneity of the powder mixture and minor fluctuations in the dispersion properties are crucial in ensuring that the inhalable proportion of active substance is released reproducibly in constant amounts and with the lowest possible variability.

Accordingly, a further aim of the present invention is to prepare an inhalable powder containing tiotropium which is characterised by a high degree of homogeneity and uniformity of dispersion. The present invention also sets out to provide an inhalable powder which allows the inhalable proportion of active substance to be administered with the lowest possible variability.

Inhalable powders containing tiotropium which conform to the requirements listed above are known for example from WO 02/30389. These inhalable powders are essentially characterised in that they contain in addition to the active substance tiotropium in the form of one of the pharmacologically acceptable salts formed from tiotropium an excipient which is obtained by mixing coarser excipient fractions with finer excipienty fractions. However, technically complex manufacturing and mixing methods are required in order to prepare these inhalable powders known from WO 02/30389. A further aim of the present invention is therefore to provide inhalable powders which not only solve the problems mentioned above but can also be obtained by an easier technical method of preparation.

The characteristics of emptying from the powder reservoir (the container from which the inhalable powder containing the active substance is released for inhalation) play an important part, not exclusively, but especially in the administration of inhalable powders using capsules containing powder. If only a small amount of the powder formulation is released from the powder reservoir as a result of minimal or poor emptying characteristics, significant amounts of the inhalable powder containing the active substance are left in the powder reservoir (e.g. the capsule) and are unavailable to the patient for therapeutic use. The result of this is that the dosage of active substance in the powder mixture has to be increased so that the quantity of active substance delivered is sufficient to produce the desired therapeutic effect.

Against this background the present invention further sets out to provide an inhalable powder which is also characterised by very good emptying characteristics.

DETAILED DESCRIPTION OF THE INVENTION

It was found that, surprisingly, the objectives outlined above can be achieved by means of the powdered preparations for inhalation (inhalable powders) according to the invention described hereinafter.

Accordingly, the present invention relates to inhalable powders containing 0.001 to 3% of tiotropium mixed with a physiologically acceptable excipient, characterised in that the excipient has an average particle size of 10-50 μm, a 10% fine content of 0.5 to 6 μm and a specific surface area of 0.1 to 2 $m^2/g$.

By the average particle size is meant here the 50% value of the volume distribution measured using a laser diffractometer by the dry dispersion method. Analogously, the 10% fine content in this instance refers to the 10% value of the volume distribution measured using a laser diffractometer. In other words, for the purposes of the present invention, the 10% fine content denotes the particle size below which 10% of the quantity of particles is found (based on the volume distribution).

By specific surface area is meant, for the purposes of the invention, the mass-specific powder surface area, calculated from the $N_2$ absorption isotherm which is observed at the boiling point of liquid nitrogen (method of Brunauer, Emmett and Teller).

Inhalable powders which contain 0.01 to 2% of tiotropium are preferred according to the invention. Particularly preferred inhalable powders contain tiotropium in an amount of about 0.03 to 1%, preferably 0.05 to 0.6%, more preferably 0.06 to 0.3%. Of particular importance according to the invention are, finally, inhalable powders which contain about 0.08 to 0.22% tiotropium.

By tiotropium is meant the free ammonium cation. Where the term active substance is used within the scope of the present invention, this should be interpreted as being a reference to tiotropium combined with a corresponding counter-ion. The counter-ion (anion) may preferably be chloride, bromide, iodide, methanesulphonate or para-toluenesulphonate. Of these anions, the bromide is preferred.

Accordingly, the present invention preferably relates to inhalable powders which contain between 0.0012 and 3.6%, preferably 0.012 to 2.4% tiotropium bromide. Of particular interest according to the invention are inhalable powders which contain about 0.036 to 1.2%, preferably 0.06 to 0.72%, more preferably 0.072 to 0.36% tiotropium bromide. Of particular interest according to the invention are inhalable powders which contain about 0.096 to 0.264% tiotropium bromide.

The tiotropium bromide which is preferably contained in the inhalable powders according to the invention may include solvent molecules during crystallisation. Preferably, the hydrates of tiotropium bromide are used to prepare the tiotropium-containing inhalable powder according to the invention. Most preferably, the crystalline tiotropium bromide monohydrate known from WO 02/30928 is used. This crystalline tiotropium bromide monohydrate is characterised by an endothermic maximum at 230±5° C. at a heating rate of 10K/min, when thermally analysed by DSC. It is also characterised in that in the IR spectrum it has bands inter alia at wavelengths 3570, 3410, 3105, 1730, 1260, 1035 and 720 $cm^{-1}$. Finally, this crystalline tiotropium bromide monohydrate has a simple monoclinic cell with the following dimensions: a=18.0774 Å, b=11.9711 Å, c=9.9321 Å, β=102.691°, V=2096.96 $Å^3$ as determined by monocrystalline X-ray structural analysis.

Accordingly the present invention relates to powders for inhalation which contain between 0.0013 and 3.75%, preferably 0.0125 to 2.5% of tiotropium bromide monohydrate. Of particular interest according to the invention are inhalable powders which contain about 0.0375 to 1.25%, preferably 0.0625 to 0.75%, more preferably 0.075 to 0.375% of tiotropium bromide monohydrate. Finally, of particular importance according to the invention are inhalable powders which contain about 0.1 to 0.275% tiotropium bromide monohydrate.

The percentages given within the scope of the present invention are always percent by weight, unless specifically stated to the contrary.

In particularly preferred inhalable powders the excipient is characterised by an average particle size of 12 to 35 μm, more preferably 13 to 30 μm. Also particularly preferred are those inhalable powders wherein the 10% fine content is about 1 to 4 μm, preferably about 1.5 to 3 μm.

Also preferred according to the invention are those inhalable powders wherein the excipient has a specific surface area of between 0.2 and 1.5 $m^2/g$, preferably between 0.3 and 1.0 $m^2/g$.

The excipients which are used for the purposes of the present invention are prepared by suitable milling and/or screening using conventional methods known in the art. In particular, the excipients used according to the invention are not mixtures of excipients obtained by mixing together excipient fractions with different average particle sizes.

Examples of physiologically acceptable excipients which may be used to prepare the inhalable powders used for the inhalettes according to the invention include, for example, monosaccharides (e.g. glucose or arabinose), disaccharides (e.g. lactose, saccharose, maltose, trehalose), oligo- and polysaccharides (e.g. dextrane), polyalcohols (e.g. sorbitol, mannitol, xylitol), or salts (e.g. sodium chloride, calcium carbonate). Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Preferably, excipients of high crystallinity are used for the powder formulations according to the invention. This crystallinity can be assessed by means of the enthalpy released as the excipient is dissolved (solution enthalpy). In the case of the excipient lactose monohydrate, which is most preferably used acording to the invention, it is preferable to use lactose which is characterised by a solution enthalpy of ≧45 J/g, preferably ≧50 J/g, particularly preferably ≧52 J/g.

The inhalable powders according to the invention are characterised, in accordance with the problem on which the invention is based, by a high degree of homogeneity in the sense of the accuracy of single doses. This is in the region of <8%, preferably <6%, most preferably <4%.

After the starting materials have been weighed in the inhalable powders are prepared from the excipient and the active substance using methods known in the art. Reference may be made to the disclosure of WO 02/30390, for example. The inhalable powders according to the invention may accordingly be obtained by the method described below, for example. In the preparation methods described hereinafter the components are used in the proportions by weight described in the above-mentioned compositions of the inhalable powders.

First, the excipient and the active substance are placed in a suitable mixing container. The active substance used has an average particle size of 0.5 to 10 µm, preferably 1 to 6 µm, most preferably 2 to 5 µm. The excipient and the active substance are preferably added using a sieve or a granulating sieve with a mesh size of 0.1 to 2 mm, preferably 0.3 to 1 mm, most preferably 0.3 to 0.6 mm. Preferably, the excipient is put in first and then the active substance is added to the mixing container. During this mixing process the two components are preferably added in batches. It is particularly preferred to sieve in the two components in alternate layers. The mixing of the excipient with the active substance may take place while the two components are still being added. Preferably, however, mixing is only done once the two components have been sieved in layer by layer.

If after being chemically prepared the active substance used in the process described above is not already obtainable in a crystalline form with the particle sizes mentioned earlier, it can be ground up into the particle sizes which conform to the above-mentioned parameters (so-called micronising).

If the active substance used is the crystalline tiotropium bromide monohydrate disclosed by WO 02/30928 which is particularly preferred according to the invention the following procedure has proved particularly suitable for micronising this crystalline active substance modification. The process may be carried out using conventional mills. Preferably, the micronisation is carried out with the exclusion of moisture, more preferably, using a corresponding inert gas such as nitrogen, for example. It has proved particularly preferable to use air jet mills in which the material is comminuted by the impact of the particles on one another and on the walls of the grinding container. According to the invention, nitrogen is preferably used as the grinding gas. The material for grinding is conveyed by the grinding gas under specific pressures (grinding pressure). Within the scope of the present invention, the grinding pressure is usually set to a value between about 2 and 8 bar, preferably between about 3 and 7 bar, most preferably between about 3.5 and 6.5 bar. The material for grinding is fed into the air jet mill by means of the feed gas under specific pressures (feed pressure). Within the scope of the present invention a feed pressure of between about 2 and 8 bar, preferably between about 3 and 7 bar and most preferably between about 3.5 and 6 bar has proved satisfactory. The feed gas used is also preferably an inert gas, most preferably nitrogen again. The material to be ground (crystalline tiotropium bromide monohydrate) may be fed in at a rate of about 5-35 g/min, preferably at about 10-30 g/min.

For example, without restricting the subject of the invention thereto, the following apparatus has proved suitable as a possible embodiment of an air jet mill: a 2-inch Microniser with grinding ring, 0.8 mm bore, made by Messrs Sturtevant Inc., 348 Circuit Street, Hanover, Mass. 02239, USA. Using the apparatus, the grinding process is preferably carried out with the following grinding parameters: grinding pressure: about 4.5-6.5 bar; feed pressure: about 4.5-6.5 bar; supply of grinding material: about 17-21 g/min.

The ground material thus obtained is then further processed under the following specific conditions. The micronisate is exposed to a water vapour at a relative humidity of at least 40% at a temperature of 15-40° C., preferably 20-35° C., most preferably 25-30° C. Preferably, the humidity is set to a value of 50-95% r. h., preferably 60-90% r.h., most preferably 70-80% r.h. By relative humidity (r.h.) is meant the quotient of the partial steam pressure and the steam pressure of the water at the temperature in question. Preferably, the micronisate obtained from the grinding process described above is subjected to the chamber conditions mentioned above for a period of at least 6 hours. Preferably, however, the micronisate is subjected to the chamber conditions mentioned above for about 12 to 48 hours, preferably about 18 to 36 hours, more preferably about 20 to 28 hours.

The micronisate of tiotropium bromide obtainable by the above method has a characteristic particle size of between 1.0 μm and 3.5 μm, preferably between 1.1 μm and 3.3 μm, most preferably between 1.2 μm and 3.0 μm and $Q_{(5.8)}$ of more than 60%, preferably more than 70%, most preferably more than 80%. The characteristic value $Q_{(5.8)}$ indicates the quantity of particles below 5.8 μm, based on the volume distribution of the particles. The particle sizes were determined within the scope of the present invention by laser diffraction (Fraunhofer diffraction). More detailed information on this subject can be found in the experimental descriptions of the invention.

Also characteristic of the tiotropium micronisate according to the invention which was prepared by the above process are Specific Surface Area values in the range between 2 $m^2/g$ and 5 $m^2/g$, more particularly between 2.5 $m^2/g$ and 4.5 $m^2/g$ and most outstandingly between 3.0 $m^2/g$ and 4.0 $m^2/g$.

A particularly preferred aspect of the present invention relates to the inhalable powders according to the invention which are characterised by a content of the tiotropium bromide monohydrate micronisate described hereinbefore.

The present invention further relates to the use of the inhalable powders according to the invention for preparing a pharmaceutical composition for the treatment of respiratory diseases, particularly for treating COPD and/or asthma.

The inhalable powders according to the invention may for example be administered using inhalers which meter a single dose from a reservoir by means of a measuring chamber (e.g. according to U.S. Pat. No. 4,570,630A) or by other means (e.g. according to DE 36 25 685 A). Preferably, however, the inhalable powders according to the invention are packed into capsules (to make so-called inhalettes), which are used in inhalers such as those described in WO 94/28958, for example.

Most preferably, the capsules containing the inhalable powder according to the invention are administered using an inhaler as shown in FIG. 1. This inhaler is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut and airholes 13 for adjusting the flow resistance.

The present invention further relates to the use of the inhalable powders according to the invention for preparing a pharmaceutical composition for treating respiratory complaints, particularly for the treatment of COPD and/or asthma, characterised in that the inhaler described above and shown in FIG. 1 is used.

For administering the inhalable powders according to the invention using powder-filled capsules it is particularly preferred to use capsules the material of which is selected from among the synthetic plastics, most preferably selected from among polyethylene, polycarbonate, polyester, polypropylene and polyethylene terephthalate. Particularly preferred synthetic plastic materials are polyethylene, polycarbonate or polyethylene terephthalate. If polyethylene is used as one of the capsule materials which is particularly preferred according to the invention, it is preferable to use polyethylene with a density of between 900 and 1000 kg/m³, preferably 940-980 kg/m³, more preferably about 960-970 kg/m³ (high density polyethylene).

The synthetic plastics according to the invention may be processed in various ways using manufacturing methods known in the art. Injection moulding of the plastics is preferred according to the invention. Injection moulding without the use of mould release agents is particularly preferred. This method of production is well defined and is characterised by being particularly reproducible.

In another aspect the present invention relates to the abovementioned capsules which contain the abovementioned inhalable powders according to the invention. These capsules may contain about 1 to 20 mg, preferably about 3 to 15 mg, most preferably about 4 to 12 mg of inhalable powder. Preferred formulations according to the invention contain 4 to 6 mg of inhalable powder. Of equivalent importance according to the invention are capsules for inhalation which contain the formulations according to the invention in an amount of from 8 to 12 mg.

Figure 1:
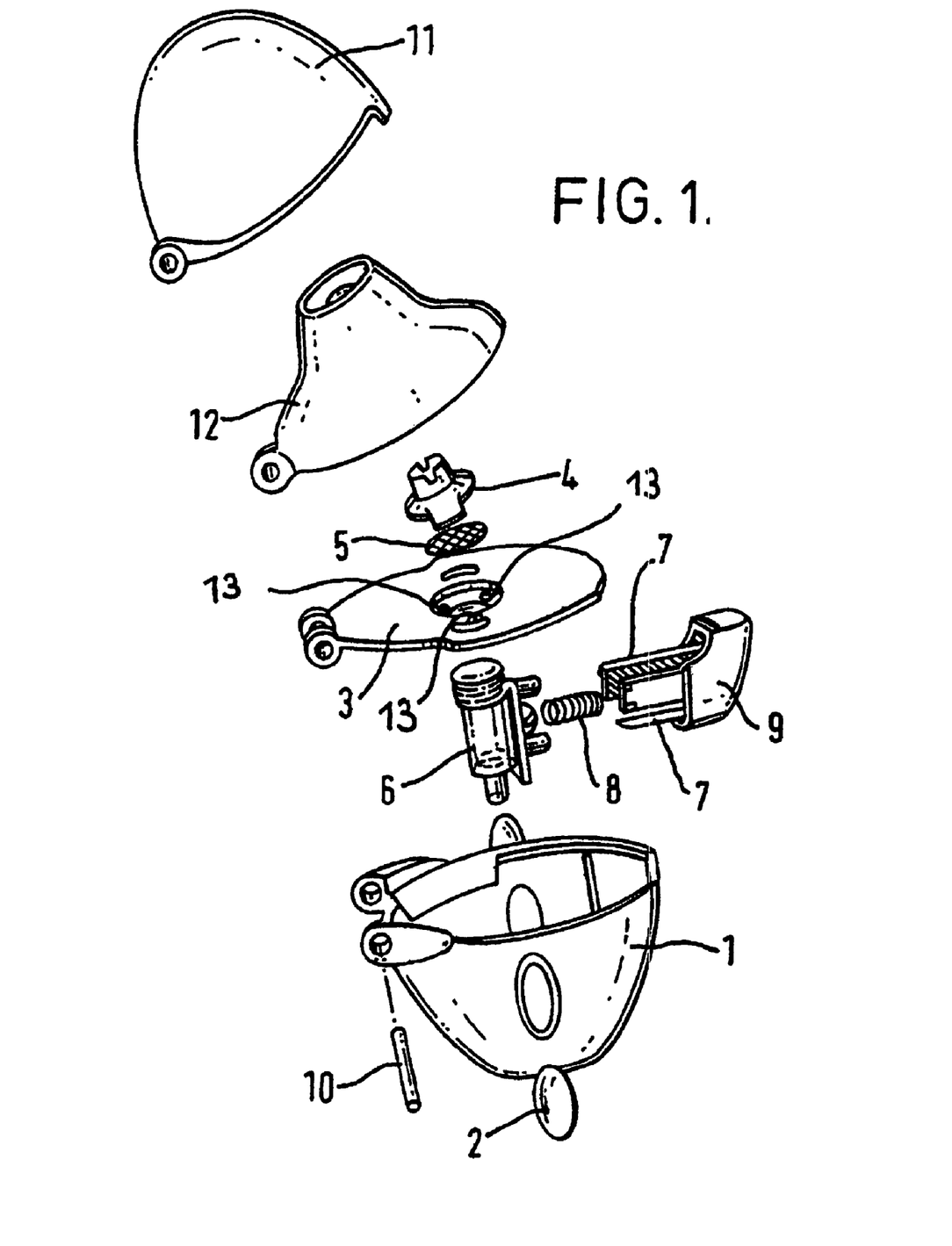

The present invention also relates to an inhalation kit consisting of one or more of the above capsules characterised by a content of inhalable powder according to the invention in conjunction with the inhaler according to FIG. 1.

The present invention also relates to the use of the abovementioned capsules characterised by a content of inhalable powder according to the invention, for preparing a pharmaceutical composition for treating respiratory complaints, especially for treating COPD and/or asthma.

Filled capsules which contain the inhalable powders according to the invention are produced by methods known in the art, by filling the empty capsules with the inhalable powders according to the invention.

The following Examples serve to illustrate the present invention in more detail without restricting the scope of the invention to the exemplifying embodiments that follow.

Starting Materials

I) Excipient:

In the Examples that follow lactose-monohydrate is used as excipient. It may be obtained for example from Borculo Domo Ingredients, Borculo/NL under the product name Lactochem Extra Fine Powder. The specifications according to the invention for the particle size and specific surface area are met by this grade of lactose. In addition, this lactose has the above-mentioned preferred solution enthalpy values for lactose according to the invention.

II) Micronisation of Crystalline Tiotropium Bromide Monohydrate:

The tiotropium bromide monohydrate obtainable according to WO 02/30928 is micronised with an air jet mill of the 2-inch microniser type with grinding ring, 0.8 mm bore, made by Messrs Sturtevant Inc., 348 Circuit Street, Hanover, Mass. 02239, USA. Using nitrogen as the grinding gas the following grinding parameters are set, for example:

grinding pressure: 5.5 bar; feed pressure: 5.5 bar; supply (of crystalline monohydrate) or flow speed: 19 g/min.

The ground material obtained is then spread out on sheet metal racks in a layer thickness of about 1 cm and subjected to the following climatic conditions for 24-24.5 hours:

temperature: 25-30° C.; relative humidity: 70-80%.

Measuring Methods:

Determining the Particle Size of Micronised Tiotropium Monohydrate:

Measuring Equipment and Settings:

The equipment is operated according to the manufacturer's instructions.

| Measuring equipment: | HELOS Laser-diffraction spectrometer, (SympaTec) |
|---|---|
| Dispersing unit: | RODOS dry disperser with suction funnel, (SympaTec) |
| Sample quantity: | 200 mg ± 150 mg |
| Product feed: | Vibri Vibrating channel, Messrs. Sympatec |
| Frequency of vibrating channel: | rising to 100% |
| Duration of sample feed: | 15 to 25 sec. (in the case of 200 mg) |
| Focal length: | 100 mm (measuring range: 0.9-175 µm) |
| Measuring time: | about 15 s (in the case of 200 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

About 200 mg of the test substance are weighed onto a piece of card. Using another piece of card all the larger lumps are broken up. The powder is then sprinkled finely over the front half of the vibrating channel (starting about 1 cm from the front edge). After the start of the measurement the frequency of the vibrating channel is varied so that the sample is fed in as continuously as possible. However, the quantity of product should not be too great either, so as to ensure adequate dispersal.

II) Determining the Particle Size of the Lactose:

Measuring Equipment and Settings:

The equipment is operated according to the manufacturer's instructions.

| Measuring equipment: | HELOS Laser-diffraction spectrometer, (SympaTec) |
|---|---|
| Dispersing unit: | RODOS dry disperser with suction funnel, (SympaTec) |
| Sample quantity: | 200 mg ± 100 mg |
| Product feed: | Vibri Vibrating channel, Messrs. Sympatec |
| Frequency of vibrating channel: | 100% rising |
| Focal length: | 200 mm (measuring range: 1.8-350 µm) |
| Measuring time: | about 10 s (in the case of 200 mg) |
| Cycle time: | 10 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed: About 200 mg of the test substance are weighed onto a piece of card. Using another piece of card all the larger lumps are broken up. The powder is transferred into the vibrating channel. A gap of 1.2 to 1.4 mm is set between the vibrating channel and funnel. After the start of the measurement the frequency of the vibrating channel is increased as continuously as possible to 100% towards the end of the measurement.

III) Determining the Specific Surface Area of Tiotropium Bromide Monohydrate, Micronised (1-Point BET Method):

Method:

The specific surface is determined by exposing the powder sample to a nitrogen/helium atmosphere at different pressures. Cooling the sample causes the nitrogen molecules to be condensed on the surface of the particles. The quantity of condensed nitrogen is determined by means of the change in the thermal heat conductivity of the nitrogen/helium mixture and the surface of the sample is calculated by means of the surface nitrogen requirement. Using this value and the weight of the sample, the specific surface is calculated.

| Equipment and materials: | |
|---|---|
| Measuring equipment: | Monosorb, Messrs Quantachrome |
| Heater: | Monotektor, Messrs Quantachrome |
| Measuring and drying gas: | nitrogen (5.0)/helium (4.6) 70/30, Messer Griesheim |
| Adsorbate: | 30% nitrogen in helium |
| Coolant: | liquid nitrogen |
| Measuring cell: | with capillary tube, Messrs. W. Pabisch GmbH&Co.KG |
| Calibration peak; | 1000 µl, Messrs. Precision Sampling Corp. |
| Analytical scale: | R 160 P, Messrs. Satorius |

Calculating the Specific Surface:

The measured values are indicated by the equipment in [m²] and are usually converted into [cm²/g] on weighing (dry mass):

$$A_{spez} = \frac{MW * 10000}{m_{tr}}$$

$A_{spez}$ = specific surface [cm²/g]

$MW$ = Measured value [m²]

$m_{tr}$ = dry mass [g]

10000 = conversion factor [cm²/m²]

IV) Determining the Specific Surface Area of the Lactose (Multi-Point BET Method):

Method:

The specific surface is determined by exposing the powder sample to a nitrogen atmosphere at different pressures. Cooling the sample causes the nitrogen molecules to be condensed on the surface of the particles. The quantity of condensed nitrogen is determined by means of the drop in pressure in the system and the specific surface of the sample is calculated by means of the surface nitrogen requirement and the weight of the sample.

The equipment is operated according to the manufacturer's instructions.

| Measuring equipment and settings: | |
|---|---|
| Measuring equipment | Tri Star Multi Point BET, Messrs Micromeritics |
| Heater: | VacPrep 061, Messrs. Micromeritics |
| Heating: | about 12 h/40° C. |
| Sample tube: | ½ inch; use filler rod |
| Analysis Condition: | 10 point BET surface 0.1 to 0.20 p/p0 |

-continued

| Measuring equipment and settings: | |
|---|---|
| Absolute P. tolerance: | 5.0 mmHg |
| rel. P. tolerance: | 5.0% |
| Evacuation rate: | 50.0 mmHg/sec. |
| Unrestricted evac f.: | 10.0 mmHg |
| Evac. time: | 0.1 hours |
| Free Space: | Lower Dewar, time: 0.5 h |
| Equilibration interv.: | 20 sec |
| Min. equl. delay: | 600 sec |
| Adsorptive: | Nitrogen |

V) Determining the Heat of Solution (Enthalpy of Solution) $E_c$:

The solution enthalpy is determined using a solution calorimeter 2225 Precision Solution Calorimeter made by Messrs. Thermometric.

The heat of solution is calculated by means of the change in temperature occurring (as a result of the dissolving process) and the system-related change in temperature calculated from the base line.

Before and after the ampoule is broken, electrical calibration is carried out with an integrated heating resistor of a precisely known power. A known heat output is delivered to the system over a set period and the jump in temperature is determined.

| Method and equipment parameters: | |
|---|---|
| Solution calorimeter: | 2225 Precision Solution Calorimeter, Messrs Thermometric |
| Reaction cell: | 100 ml |
| Thermistor resistance: | 30.0 kΩ (at 25° C.) |
| Speed of stirrer: | 500 U/min |
| Thermostat: | Thermostat of 2277 Thermal Activity Monitor TAM, Messrs Thermometric |
| Temperature: | 25° C. ± 0.0001° C. (over 24 h) |
| Measuring ampoules: | Crushing ampoules 1 ml, Messrs Thermometric |
| Seal: | Silicon stopper and beeswax, Messrs. Thermometric |
| Weight: | 40 to 50 mg |
| Solvent: | Chemically pure water |
| Volume of solvent: | 100 ml |
| Bath temperature: | 25° C. |
| Temperature resolution: | High |
| Starting temperature: | −40 mK (± 10 mK) temperature-offset |
| Interface: | 2280-002 TAM accessory interface 50 Hz, Messrs Thermometric |
| Software: | SolCal V 1.1 for WINDOWS |
| Evaluation: | Automatic evaluation with Menu point CALCULATION/ANALYSE EXPERIMENT. (Dynamics of base line; calibration after breakage of ampoule). |

Electrical Calibration:

The electrical calibration takes place during the measurement, once before and once after the breakage of the ampoule. The calibration after the breakage of the ampoule is used for the evaluation.

| | |
|---|---|
| Amount of heat: | 2.5 J |
| Heating power: | 500 mW |

-continued

| | |
|---|---|
| Heating time: | 10 s |
| Duration of base lines: | 5 min |
| | (before and after heating) |

Preparation of the Powder Formulations According to the Invention:

I) Apparatus

The following machines and equipment, for example, may be used to prepare the inhalable powders:

Mixing container or powder mixer: Turbulamischer 2 L, Type 2C; made by Willy A. Bachofen AG, CH-4500 Basel Hand-held screen: 0.135 mm mesh size The empty inhalation capsules may be filled with inhalable powders containing tiotropium by hand or mechanically. The following equipment may be used.

Capsule Filling Machine:

MG2, Type G100, manufacturer: MG2 S.r.1, I-40065 Pian di Macina di Pianoro (BO), Italy

EXAMPLE 1

Powder Mixture:

To prepare the powder mixture, 299.39 g of excipient and 0.61 g of micronised tiotropium bromide-monohydrate are used. In the resulting 300 g of inhalable powder the content of active substance is 0.2% (based on tiotropium).

About 40-45 g of excipient are placed in a suitable mixing container through a hand-held screen with a mesh size of 0.315 mm. Then tiotropium bromide-monohydrate in batches of about 90-110 mg and excipient in batches of about 40-45 g are screened in in alternate layers. The excipient and active substance are added in 7 and 6 layers, respectively.

Having been screened in, the ingredients are then mixed (mixing speed 900 rpm). The final mixture is passed twice more through a hand-held screen and then mixed again at 900 rpm.

Using the method described in Example 1 it is possible to obtain inhalable powders which when packed into suitable plastic capsules may be used to produce the following capsules for inhalation, for example:

EXAMPLE 2

| | |
|---|---|
| tiotropium bromide monohydrate: | 0.0113 mg |
| lactose monohydrate*): | 5.4887 mg |
| polyethylene capsules: | 100.0 mg |
| Total: | 105.5 mg |
| *)the excipient is characterised by the following parameters: | |
| average particle size: | 17.9 μm; |
| 10% fine content: | 2.3 μm; |
| specific surface: | 0.61 m²/g; |

EXAMPLE 3

| | |
|---|---|
| tiotropium bromide monohydrate: | 0.0113 mg |
| lactose monohydrate*): | 5.4887 mg |
| polyethylene capsules: | 100.0 mg |
| Total: | 105.5 mg |
| *)the excipient is characterised by the following parameters: | |
| average particle size: | 18.5 μm; |
| 10% fine content: | 2.2 μm; |
| specific surface: | 0.83 m²/g; |

EXAMPLE 4

| | |
|---|---|
| tiotropium bromide monohydrate: | 0.0113 mg |
| lactose monohydrate*): | 5.4887 mg |
| polyethylene capsules: | 100.0 mg |
| Total: | 105.5 mg |
| *)the excipient is characterised by the following parameters: | |
| average particle size: | 21.6 μm; |
| 10% fine content: | 2.5 μm; |
| specific surface: | 0.59 m²/g; |

EXAMPLE 5

| | |
|---|---|
| tiotropium bromide monohydrate: | 0.0113 mg |
| lactose monohydrate*): | 5.4887 mg |
| polyethylene capsules: | 100.0 mg |
| Total: | 105.5 mg |
| *)the excipient is characterised by the following parameters: | |
| average particle size: | 16.0 μm; |
| 10% fine content: | 2.0 μm; |
| specific surface: | 0.79 m²/g; |

EXAMPLE 6

| | |
|---|---|
| tiotropium bromide monohydrate: | 0.0225 mg |
| lactose monohydrate*): | 5.4775 mg |
| polyethylene capsules: | 100.0 mg |
| Total: | 105.5 mg |
| *)the excipient is characterised by the following parameters: | |
| average particle size: | 17.9 μm; |
| 10% fine content: | 2.3 μm; |
| specific surface: | 0.61 m²/g; |

EXAMPLE 7

| | |
|---|---|
| tiotropium bromide monohydrate: | 0.0225 mg |
| lactose monohydrate*): | 5.4775 mg |
| polyethylene capsules: | 100.0 mg |
| Total: | 105.5 mg |

*) the excipient is characterised by the following parameters:
average particle size: 18.5 μm;
10% fine content: 2.2 μm;
specific surface: 0.83 m$^2$/g;

EXAMPLE 8

| | |
|---|---|
| tiotropium bromide monohydrate: | 0.0225 mg |
| lactose monohydrate*): | 5.4775 mg |
| polyethylene capsules: | 100.0 mg |
| Total: | 105.5 mg |

*) the excipient is characterised by the following parameters:
average particle size: 21.6 μm;
10% fine content: 2.5 μm;
specific surface: 0.59 m$^2$/g;

EXAMPLE 9

| | |
|---|---|
| tiotropium bromide monohydrate: | 0.0225 mg |
| lactose monohydrate*): | 5.4775 mg |
| polyethylene capsules: | 100.0 mg |
| Total: | 105.5 mg |

*) the excipient is characterised by the following parameters:
average particle size: 16.0 μm;
10% fine content: 2.0 μm;
specific surface: 0.79 m$^2$/g;

EXAMPLE 10

| | |
|---|---|
| tiotropium bromide monohydrate: | 0.0056 mg |
| lactose monohydrate*): | 5.4944 mg |
| polyethylene capsules: | 100.0 mg |
| Total: | 105.5 mg |

*) the excipient is characterised by the following parameters:
average particle size: 17.9 μm;
10% fine content: 2.3 μm;
specific surface: 0.61 m$^2$/g;

EXAMPLE 11

| | |
|---|---|
| tiotropium bromide monohydrate: | 0.0056 mg |
| lactose monohydrate*): | 5.4944 mg |
| polyethylene capsules: | 100.0 mg |
| Total: | 105.5 mg |

*) the excipient is characterised by the following parameters:
average particle size: 18.5 μm;
10% fine content: 2.2 μm;
specific surface: 0.83 m$^2$/g;

EXAMPLE 12

| | |
|---|---|
| tiotropium bromide monohydrate: | 0.0056 mg |
| lactose monohydrate*): | 5.4944 mg |
| polyethylene capsules: | 100.0 mg |
| Total: | 105.5 mg |

*) the excipient is characterised by the following parameters:
average particle size: 21.6 μm;
10% fine content: 2.5 μm;
specific surface: 0.59 m$^2$/g;

EXAMPLE 13

| | |
|---|---|
| tiotropium bromide monohydrate: | 0.0056 mg |
| lactose monohydrate*): | 5.4944 mg |
| polyethylene capsules: | 100.0 mg |
| Total: | 105.5 mg |

*) the excipient is characterised by the following parameters:
average particle size: 16.0 μm;
10% fine content: 2.0 μm;
specific surface: 0.79 m$^2$/g;

EXAMPLE 14

| | |
|---|---|
| tiotropium bromide monohydrate: | 0.0056 mg |
| lactose monohydrate*): | 9.9944 mg |
| polyethylene capsules: | 100.0 mg |
| Total: | 110.0 mg |

*) the excipient is characterised by the following parameters:
average particle size: 17.9 μm;
10% fine content: 2.3 μm;
specific surface: 0.61 m$^2$/g;

EXAMPLE 15

| | |
|---|---|
| tiotropium bromide monohydrate: | 0.0113 mg |
| lactose monohydrate*): | 9.9887 mg |
| polyethylene capsules: | 100.0 mg |
| Total: | 110.0 mg |

*)the excipient is characterised by the following parameters:
average particle size: 18.5 μm;
10% fine content: 2.2 μm;
specific surface: 0.83 m$^2$/g;

EXAMPLE 16

| | |
|---|---|
| tiotropium bromide monohydrate: | 0.0225 mg |
| lactose monohydrate*): | 9.9775 mg |
| polyethylene capsules: | 100.0 mg |
| Total: | 110.0 mg |

*)the excipient is characterised by the following parameters:
average particle size: 21.6 μm;
10% fine content: 2.5 μm;
specific surface: 0.59 m$^2$/g;

EXAMPLE 17

| | |
|---|---|
| tiotropium bromide monohydrate: | 0.0125 mg |
| lactose monohydrate*): | 9.9875 mg |
| polyethylene capsules: | 100.0 mg |
| Total: | 110.0 mg |

*)the excipient is characterised by the following parameters:
average particle size: 17.9 μm;
10% fine content: 2.3 μm;
specific surface: 0.61 m$^2$/g;

EXAMPLE 18

| | |
|---|---|
| tiotropium bromide monohydrate: | 0.0125 mg |
| lactose monohydrate*): | 9.9875 mg |
| polyethylene capsules: | 100.0 mg |
| Total: | 110.0 mg |

*)the excipient is characterised by the following parameters:
average particle size: 18.5 μm;
10% fine content: 2.2 μm;
specific surface: 0.83 m$^2$/g;

EXAMPLE 19

| | |
|---|---|
| tiotropium bromide monohydrate: | 0.0125 mg |
| lactose monohydrate*): | 9.9875 mg |
| polyethylene capsules: | 100.0 mg |
| Total: | 110.0 mg |

*)the excipient is characterised by the following parameters:
average particle size: 21.6 μm;
10% fine content: 2.5 μm;
specific surface: 0.59 m$^2$/g;

EXAMPLE 20

| | |
|---|---|
| tiotropium bromide monohydrate: | 0.0125 mg |
| lactose monohydrate*): | 9.9875 mg |
| polyethylene capsules: | 100.0 mg |
| Total: | 110.0 mg |

*)the excipient is characterised by the following parameters:
average particle size: 16.0 μm;
10% fine content: 2.0 μm;
specific surface: 0.79 m$^2$/g;

The invention claimed is:

1. An inhalable powder composition comprising 0.001 to 3% of tiotropium, or a pharmaceutically acceptable salt thereof, in admixture with a physiologically acceptable excipient having an average particle size of 10-50 μm, a 10% fine content of 0.5 to 6 μm and a specific surface of 0.1 to 2 m$^2$/g, wherein the physiologically acceptable excipient is lactose monohydrate characterized by a solution enthalpy of $\geq$50 J/g and wherein the excipient is not a mixture of excipients obtained by mixing together excipient fractions with different average particle sizes.

2. The composition according to claim 1 wherein the tiotropium is present as a salt in the form of the chloride, bromide, iodide, methanesulphonate or para-toluenesulphonate.

* * * * *